United States Patent
Tsubata

(10) Patent No.: US 7,195,596 B2
(45) Date of Patent: Mar. 27, 2007

(54) PULSE WAVE DETECTING APPARATUS AND FOURIER TRANSFORM PROCESS APPARATUS

(75) Inventor: Keisuke Tsubata, Chiba (JP)

(73) Assignee: Seiko Instruments Inc. (JP)

( * ) Notice: Subject to any disclaimer, the term of this patent is extended or adjusted under 35 U.S.C. 154(b) by 280 days.

(21) Appl. No.: 10/659,508

(22) Filed: Sep. 10, 2003

(65) Prior Publication Data

US 2004/0086060 A1   May 6, 2004

(30) Foreign Application Priority Data

Oct. 4, 2002  (JP)  .............................. 2002-291895

(51) Int. Cl.
*A61B 5/02*   (2006.01)
*A61B 5/00*   (2006.01)
(52) U.S. Cl. ....................................... 600/500; 600/336
(58) Field of Classification Search ........ 600/500–503, 600/322–341; 708/403–405, 445, 821; 375/316
See application file for complete search history.

(56) References Cited

U.S. PATENT DOCUMENTS 5,941,837 A * 8/1999 Amano et al. ............... 600/595
6,331,159 B1 * 12/2001 Amano et al. ............... 600/300
6,361,501 B1 * 3/2002 Amano et al. ............... 600/500
6,393,311 B1 * 5/2002 Edgar et al. ................. 600/323

FOREIGN PATENT DOCUMENTS

JP       63277034       11/1988
JP       10258039        9/1998

* cited by examiner

*Primary Examiner*—Charles A Marmor, II
*Assistant Examiner*—Navin Natnithithadha
(74) *Attorney, Agent, or Firm*—Adams & Wilks

(57) ABSTRACT

A pulse wave detecting apparatus is provided which is capable of measuring a pulse rate more accurately even with a calculation unit having low calculating capability. An A-D conversion circuit samples a pulse wave detected by a pulse wave sensor at 16 Hz to perform A-D conversion of the same and sequentially outputs resultant signals to a modified moving average process circuit. The modified moving average process circuit sequentially averages every two of the signals from the A-D conversion circuit without duplication and outputs signals at 8 Hz, and an FFT circuit performs Fourier transform on signals obtained through the averaging. Another A-D conversion circuit samples kinetic noises detected by an acceleration sensor at 8 Hz to perform A-D conversion of the same and sequentially outputs resultant signals to another FFT circuit, and the FFT circuit performs Fourier transform on the input signals. A pulse rate calculation circuit obtains differences between the signals output by the FFT circuits to calculate a pulse rate. The pulse rate is displayed by a display section.

4 Claims, 8 Drawing Sheets

● BEFORE MODIFIED MOVING AVERAGE PROCESS (=Yt)
●----● AFTER MODIFIED MOVING AVERAGE PROCESS

PULSE WAVE DETECTING APPARATUS AND FOURIER TRANSFORM PROCESS APPARATUS

BACKGROUND OF THE INVENTION

1. Field of the Invention

The present invention relates to a pulse wave detecting apparatus having a function of detecting a pulse wave of a subject and a Fourier transform process apparatus that is suitable for the pulse wave detecting apparatus.

2. Description of the Related Art

Pulse wave detecting apparatus having a function of detecting a pulse wave of a subject have been developed. A pulse wave detecting apparatus has a configuration in which a detecting section is attached to the body of a subject, a pulse wave detected by the detecting section is sampled, and signals resulting from the sampling are subjected to a Fourier transform process to acquire vital information of the subject such as the pulse rate and blood pressure.

Methods of detecting a pulse wave include a method in which a pulse wave is detected using light, a method in which a pulse wave is detected by detecting the pressure of a blood stream with a piezoelectric element, and a method in which a pulse wave is detected by applying an ultrasonic wave generated by a piezoelectric element to an artery to detect a Doppler wave generated by a blood stream.

In any of the above-mentioned methods, a pulse signal acquired by a detecting section is very small and susceptible to various noises such as noises resulting from movements of a body (kinetic noises), which results in a problem in that it is difficult to acquire accurate vital information such as a pulse rate from a pulse wave detected by the detecting section.

A method for solving this problem is to reduce the influence of noises by obtaining moving averages of sampled signals (see Article 1*, for example). According to this method, since noise components are leveled, the influence of noises can be reduced by performing a Fourier transform process on moving-averaged signals to acquire more accurate vital information.

*Article 1: Japanese Patent Laid-Open JP-A-6-197891

However, since the number of moving-averaged data is equal to the number of data before the averaging, an increase in the number of data to be Fourier-transformed increases loads on a calculation unit to perform the Fourier transform.

Therefore, in the case of apparatus such as small apparatus having a calculation unit with low calculating capability, a problem arises in that the accuracy of measurement is low because a sampling frequency cannot be set sufficiently high.

It is an object of the invention to provide a pulse wave detecting apparatus capable of measuring a pulse rate more accurately even with a calculation unit having low calculating capability.

It is another object of the invention to provide a Fourier transform process apparatus that is suitable for the pulse wave detecting apparatus.

SUMMARY OF THE INVENTION

The invention provides a Fourier transform processing apparatus comprising a sampling process unit for sampling input signals at a first frequency and sequentially outputting resultant signals, an averaging process unit for sequentially averaging every predetermined number of signals from the sampling process unit and sequentially outputting resultant signals at a second frequency, and a Fourier transform process unit for performing a Fourier transform process on the signals from the averaging process unit. The sampling process unit samples input signals at a first frequency and sequentially outputs resultant signals. The averaging process unit sequentially averages every predetermined number of signals from the sampling process unit and sequentially outputs resultant signals at a second frequency. The Fourier transform process unit performs a Fourier transform process on the signals from the averaging process unit.

A configuration may be employed in which the first frequency is n times (n is an integer equal to or greater than 2) the second frequency and in which the averaging process unit averages every n signals from the sampling process unit in the order of input and sequentially outputs signals obtained through the averaging.

A configuration may be employed in which the second frequency is $2^m$ Hz (m is a positive integer).

The invention also provides a pulse wave detecting apparatus comprising a signal detecting unit for detecting a pulse wave and outputting pulse signals associated therewith, a signal sampling process unit for sampling the pulse signals from the signal detecting unit at a first frequency and sequentially outputting resultant signals, an averaging process unit for sequentially averaging every predetermined number of signals from the signal sampling process unit and sequentially outputting resultant signals at a second frequency, a signal Fourier transform process unit for performing a Fourier transform process on the signals from the averaging process unit, and a pulse rate calculation process unit for calculating a pulse rate based on the result of the process at the signal Fourier transform process unit.

The signal detecting unit detects a pulse wave and outputs pulse signals associated therewith. The signal sampling process unit samples the pulse signals from the signal detecting unit at a first frequency and sequentially outputs resultant signals. The averaging process unit sequentially averages every predetermined number of signals from the signal sampling process unit and sequentially outputs resultant signals at a second frequency. The signal Fourier transform process unit performs a Fourier transform process on the signals from the averaging process unit. The pulse rate calculating process unit calculates a pulse rate based on the result of the process at the signal Fourier transform process unit.

A configuration may be employed which includes a noise detecting unit for detecting kinetic noises and outputting noise signals associated therewith, a noise sampling process unit for sampling the noise signals from the noise detecting unit at the second frequency and sequentially outputting resultant signals, and a noise Fourier transform process unit for performing a Fourier transform process on the signals from the noise sampling process unit and in which the pulse rate calculation process unit calculates a pulse rate based on the signals output by the signal Fourier transform process unit and the noise Fourier transform process unit.

A configuration may be employed in which the first frequency is n times (n is an integer equal to or greater than 2) the second frequency and in which the averaging process unit averages every n signals from the signal sampling process unit in the order of input and sequentially outputs signals obtained through the averaging.

A configuration may be employed in which the second frequency is $2^m$ Hz (m is a positive integer).

DESCRIPTION OF THE PREFERRED EMBODIMENT

Figure 1:
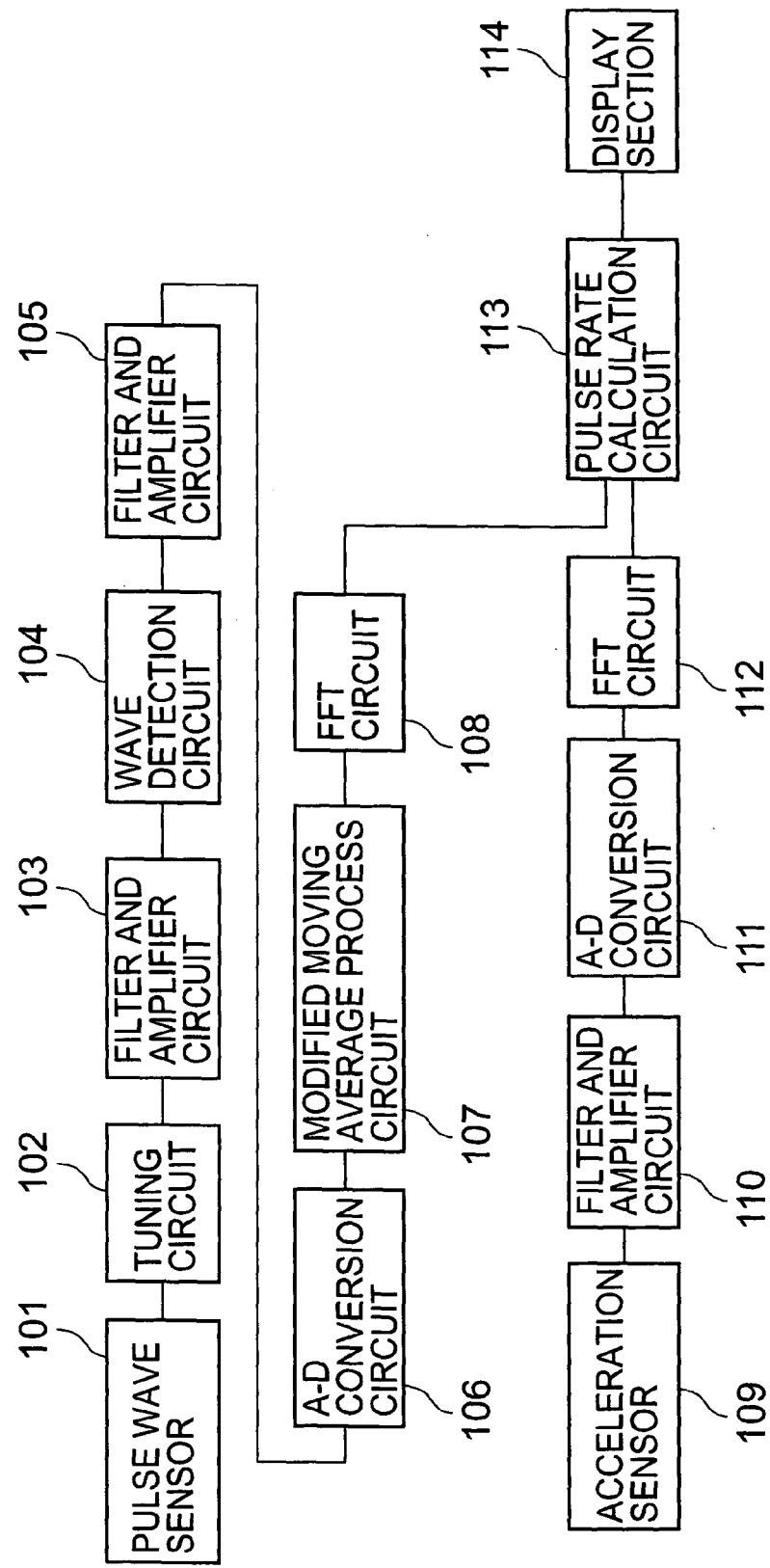
FIG. 1 is a block diagram of a pulse wave detecting apparatus and a Fourier transform process apparatus according to an embodiment of the invention.

A preferred form of the present invention is illustrated in the accompanying drawings in which:

FIG. 1 is a block diagram of a pulse wave detecting apparatus according to an embodiment of the invention.

In FIG. 1, the pulse wave detecting apparatus has a pulse wave sensor 101 as a signal detecting unit that detects a pulse wave of a subject and outputs pulse signals associated therewith, a tuning circuit 102 that extracts pulse signal components in the signals output by the pulse wave sensor 101, a filter and amplifier circuit 103 that amplifies signals having a predetermined frequency in signals output by the tuning circuit 102 and allows them to pass, a wave detection circuit 104 that detects signals output by the filter and amplifier circuit 103, a filter and amplifier circuit 105 that amplifies signals having a predetermined frequency among signals output by the wave detection circuit 104, and allows them to pass an A-D conversion circuit 106 as a signal sampling process unit that samples analog output signals from the filter and amplifier circuit 105 and converts them into digital signals, a modified moving average process circuit 107 as an averaging process unit that performs an averaging process as will be described later on signals output by the A-D conversion circuit 106, and an FFT circuit 108 as a signal Fourier transform process unit that performs a fast Fourier transform (FFT) process on signals from the modified moving average process circuit 107.

The pulse wave detecting apparatus also has an acceleration sensor 109 as a noise detecting unit that detects noises generated by movements of the body of a subject (kinetic noises) and outputs noise signals associated therewith, a filter and amplifier circuit 110 that amplifies signals having a predetermined frequency among the signals output by the acceleration sensor 109 and allows them to pass, an A-D conversion circuit 111 as a noise sampling process unit that samples analog output signals from the filter and amplifier circuit 110 and converts them into digital signals, and an FFT circuit 112 as a noise Fourier transform process unit that performs a fast Fourier transform (FFT) process on signals output by the A-D conversion circuit 111.

The pulse wave detecting apparatus has a pulse rate calculating circuit 113 as a pulse rate calculation process unit that obtains a difference between a signal output by the FFT circuit 108 and a signal output by the FFT circuit 112 and calculates a pulse rate based on the difference signal and a display section 114 as a display unit that displays the pulse rate calculated by the pulse rate calculating circuit 113.

The pulse wave sensor 101 is used by attaching the same to the body (a wrist, for example) of a subject to detect an arterial wave, and various sensors such as optical sensors and piezoelectric elements may be used depending on methods of detection. In the case of a method of detecting a pulse wave utilizing a Doppler effect of an ultrasonic wave, the pulse wave sensor 101 is constituted by a piezoelectric element for transmitting an ultrasonic wave and a piezoelectric element for receiving an ultrasonic wave, and an ultrasonic wave transmission/reception circuit for transmitting and receiving an ultrasonic wave is used.

Further, the acceleration sensor 109 is used by attaching the same to the body in the vicinity of the pulse wave sensor 101.

The A-D conversion circuit 106, the modified moving average process circuit 107, and the FFT circuit 108 constitute a Fourier transform process apparatus.

Figure 2:
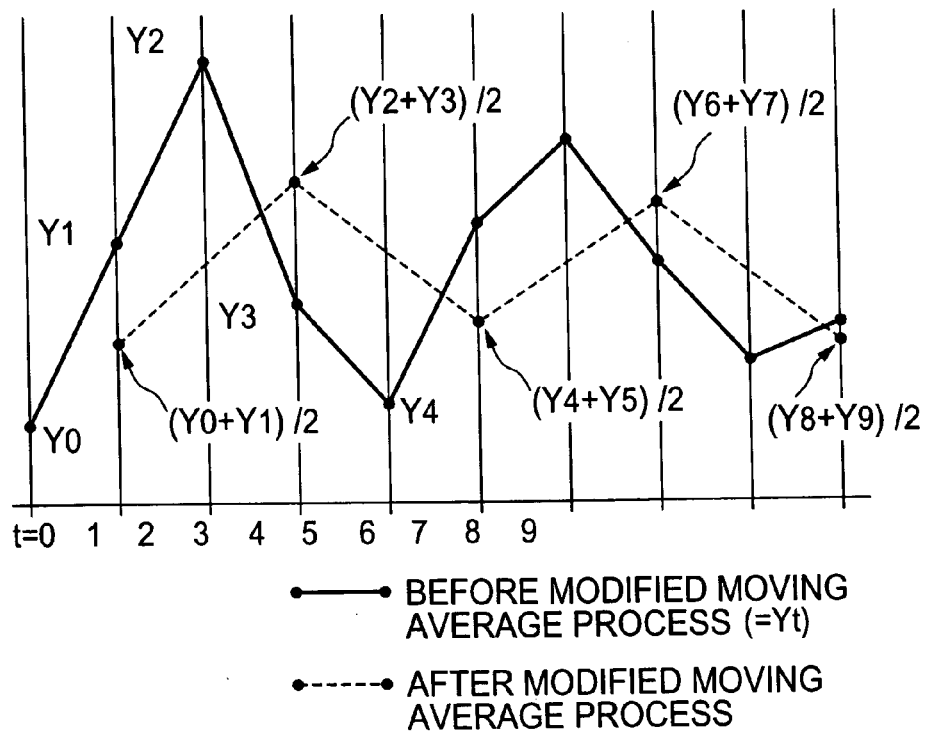
FIG. 2 is a waveform diagram for explaining a process in the embodiment of the invention.

FIG. 2 is a graph for explaining the process at the modified moving average process circuit 107. In FIG. 2, points Y0, Y1, Y2, and so on connected by a solid line represent signals that have been sampled and digitized by the A-D conversion circuit 106 and signals output by the A-D conversion circuit 106. In the present embodiment, a sampling frequency of 16 Hz is used at the A-D conversion circuit 106, for example.

The modified moving average process circuit 107 sequentially averages every two of the signals Y0, Y1, and so on output by the A-D conversion circuit 106 without duplication (the process being referred to as "modified moving average") to calculate and output (Y0+Y1)/2, (Y2+Y3)/2, and so on. The modified moving average process circuit 107 outputs digital output signals (Y0+Y1)/2, (Y2+Y3)/2, and so on having a frequency (8 Hz in the present embodiment) that is one half of the sampling frequency of the A-D conversion circuit 106 as indicated by the broken line.

Figure 3:
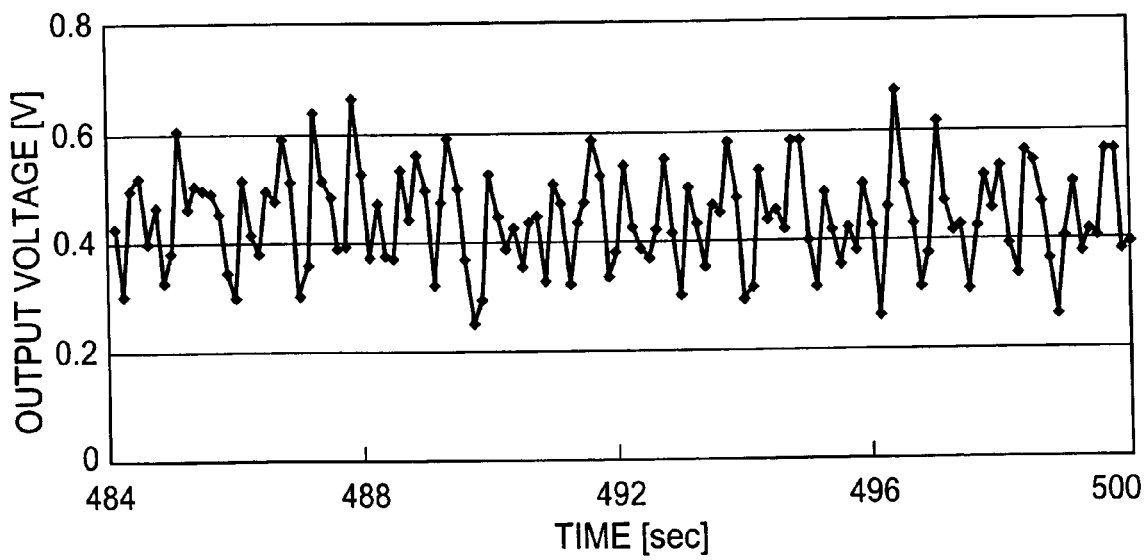
FIG. 3 is a waveform diagram for explaining a process in the embodiment of the invention.
Figure 4:
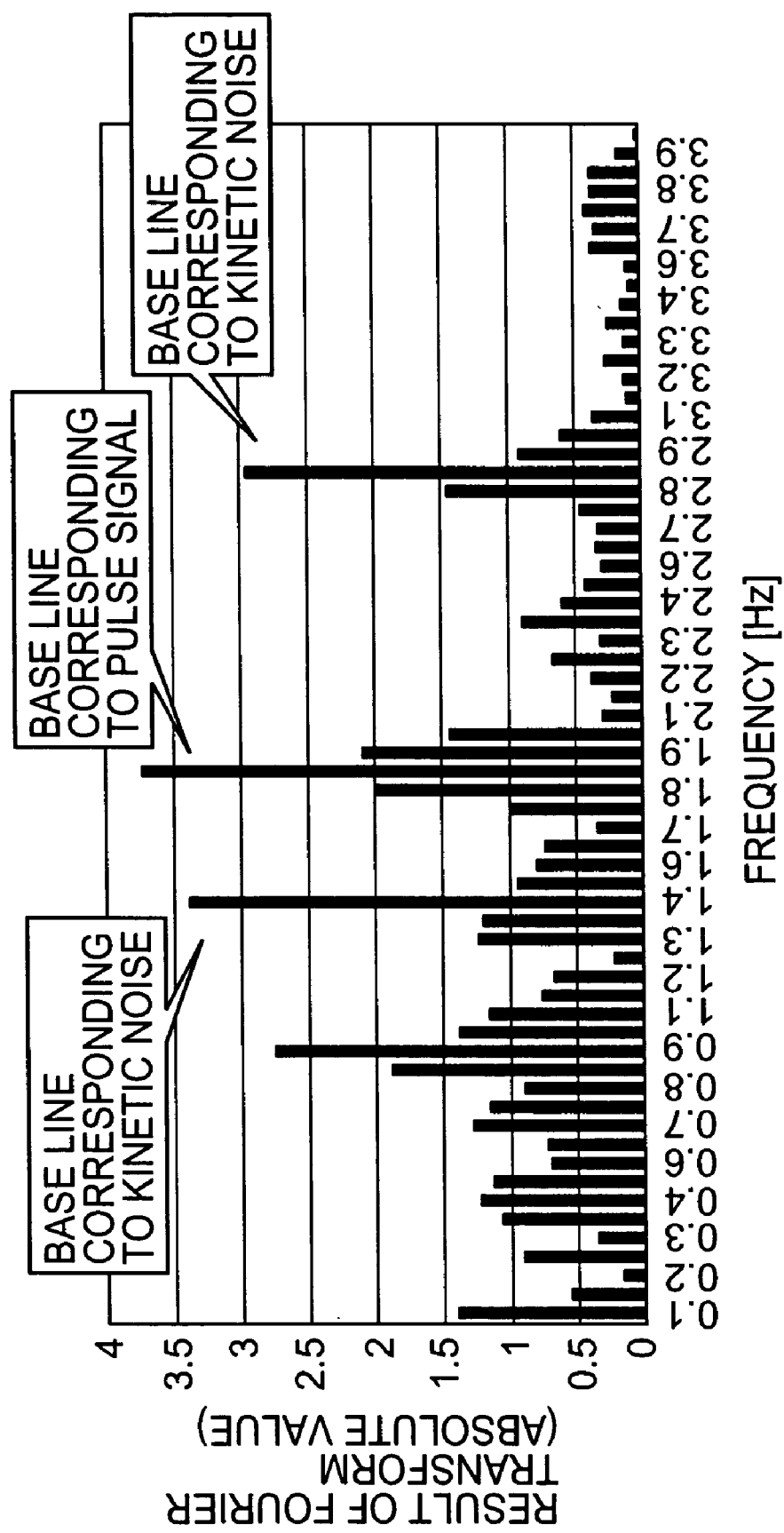
FIG. 4 is a waveform diagram for explaining a process in the embodiment of the invention.
Figure 5:
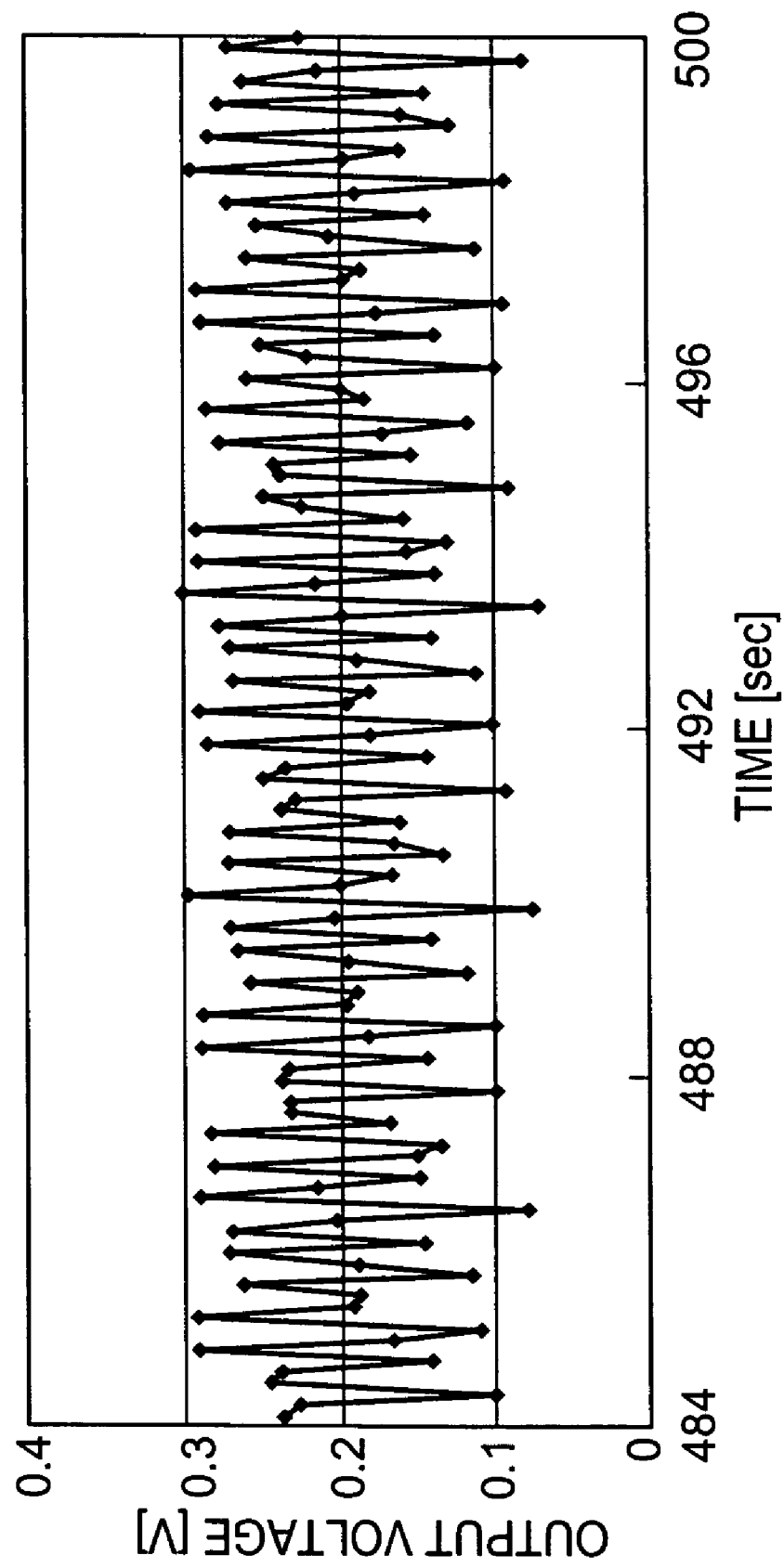
FIG. 5 is a waveform diagram for explaining a process in the embodiment of the invention.
Figure 6:
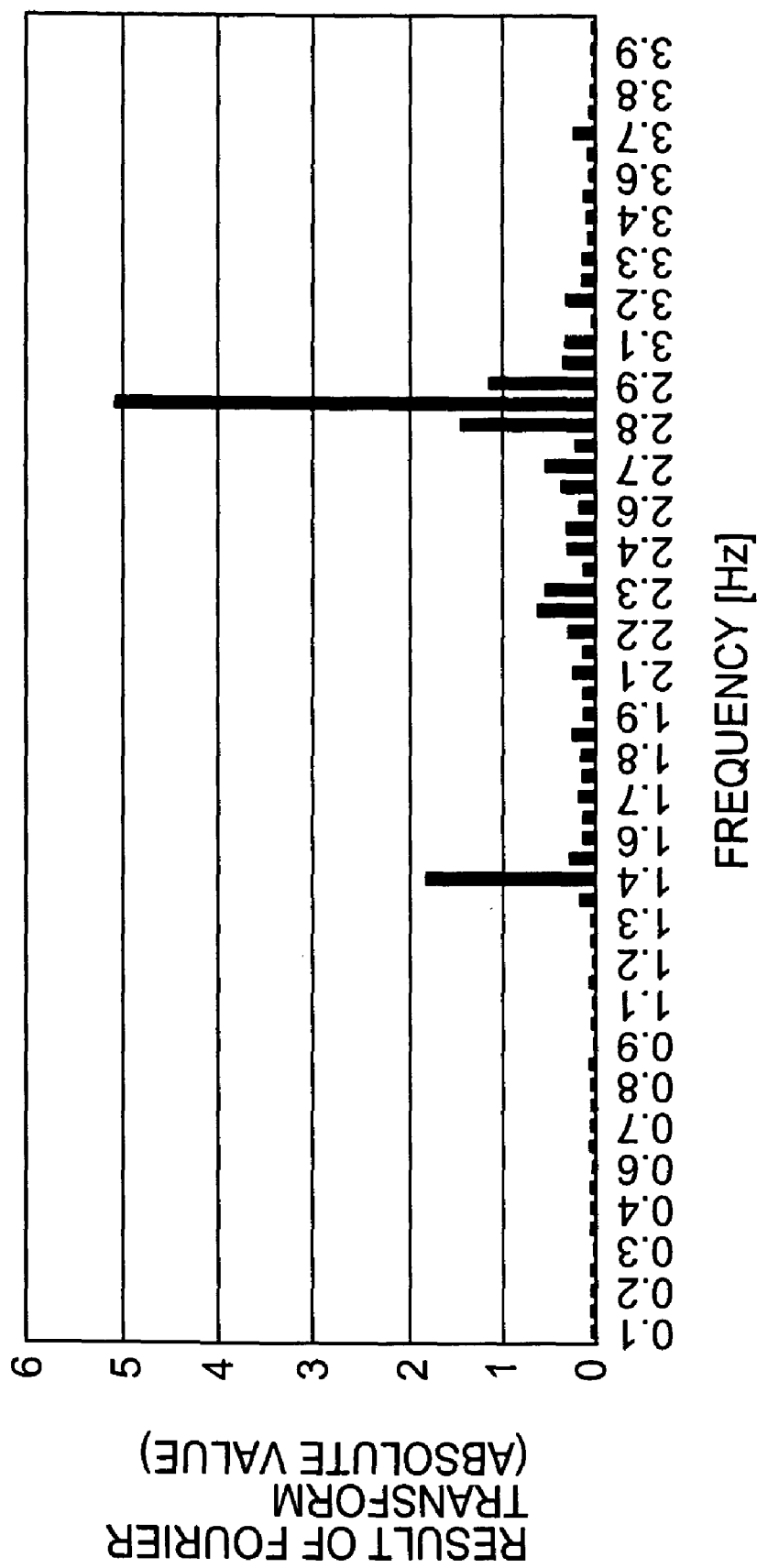
FIG. 6 is a waveform diagram for explaining a process in the embodiment of the invention.

FIG. 3 shows signals output by the modified moving average process circuit 107. FIG. 4 shows signals output by the FFT circuit 108. FIG. 5 shows signals output by the A-D conversion circuit 111. FIG. 6 shows signals output by the FFT circuit 112.

Operations of the pulse wave detecting apparatus and the Fourier transform process apparatus according to the present embodiment will now be described in detail with reference to FIGS. 1 to 6.

When attached to the body of a subject (a wrist, for example), the pulse wave sensor 101 detects a pulse wave of the subject and outputs pulse signals associated therewith. The tuning circuit 102 extracts signals in the frequency range of pulse signal components from the signals output by the pulse wave sensor 101 and outputs them. The filter and amplifier circuit 103 amplifies signals having a predetermined frequency among the signals output by the tuning circuit 102 and allows them to pass. The wave detection circuit 104 detects the signals output by the filter and amplifier circuit 103 and outputs them to the filter and amplifier circuit 105. The filter and amplifier circuit 105 amplifies signals having a predetermined frequency among the signals output by the wave detection circuit 104 and allows them to pass.

The A-D conversion circuit 106 samples analog output signals from the filter and amplifier circuit 105 at a predetermined frequency (16 Hz in the present embodiment) and converts them into digital signals that are output to the modified moving average process circuit 107. As shown in FIG. 2, the modified moving average process circuit 107 sequentially averages every predetermined number (two in the present embodiment) of the digital signals in the order of input without duplication and outputs signals obtained through the averaging to the FFT circuit 108. Thus, modified moving average signals at 8 Hz are sequentially output by the modified moving average process circuit 107 as shown in FIG. 3.

The FFT circuit 108 performs a digital Fourier transform (FFT) process on the signals from the modified moving average process circuit 107 and outputs FFT-processed signals (FFT pulse signals) as shown in FIG. 4. The signals output by the FFT circuit 108 include a base line corresponding to a pulse signal and base lines corresponding to kinetic noises, as shown in FIG. 4.

The acceleration sensor 109 that is attached to the body of the subject (a wrist, for example) in the vicinity of the pulse wave sensor 101 detects movements of the subjects and outputs kinetic noises associated therewith. The filter and amplifier circuit 110 amplifies signals having a predetermined frequency among the signals output by the acceleration sensor 109 and allows them to pass.

As shown in FIG. 5, the A-D conversion circuit 111 samples analog output signals from the filter and amplifier circuit 110 at a predetermined frequency and converts them into digital signals that are output to the FFT circuit 112. In the present embodiment, the sampling frequency of the A-D conversion circuit 111 is set at 8 Hz. That is, the sampling frequency of the A-D conversion circuit 106 is set at twice the sampling frequency of the A-D conversion circuit 111. The sampling frequency of the A-D conversion circuit 111 is set equal to the frequency of the signals output by the modified moving average process circuit 107, which makes it possible to easily reduce the influence of noise components such as kinetic noises when the pulse rate calculation circuit 113 calculates a pulse rate.

The FFT circuit 112 performs a digital Fourier transform (FFT) process on noise signals from the A-D conversion circuit 111 and outputs FFT-processed signals (FFT noise signals) as shown in FIG. 6. The signals output by the FFT circuit 112 include no base line corresponding to a pulse signal but include base lines corresponding to kinetic noises as shown in FIG. 6.

The pulse rate calculation circuit 113 obtains differences between the signals output by the FFT circuit 108 and the signals output by the FFT circuit 112 (differences between the signals in FIGS. 4 and 6) to acquire signals associated with pulse signals that are less susceptible to noises such as kinetic noises. Next, the pulse rate calculation circuit 113 calculates the pulse rate of the subject based on a center frequency of the signals thus obtained and outputs a signal indicating the pulse rate to the display section 114. The display section 114 displays the pulse rate.

Figure 7:
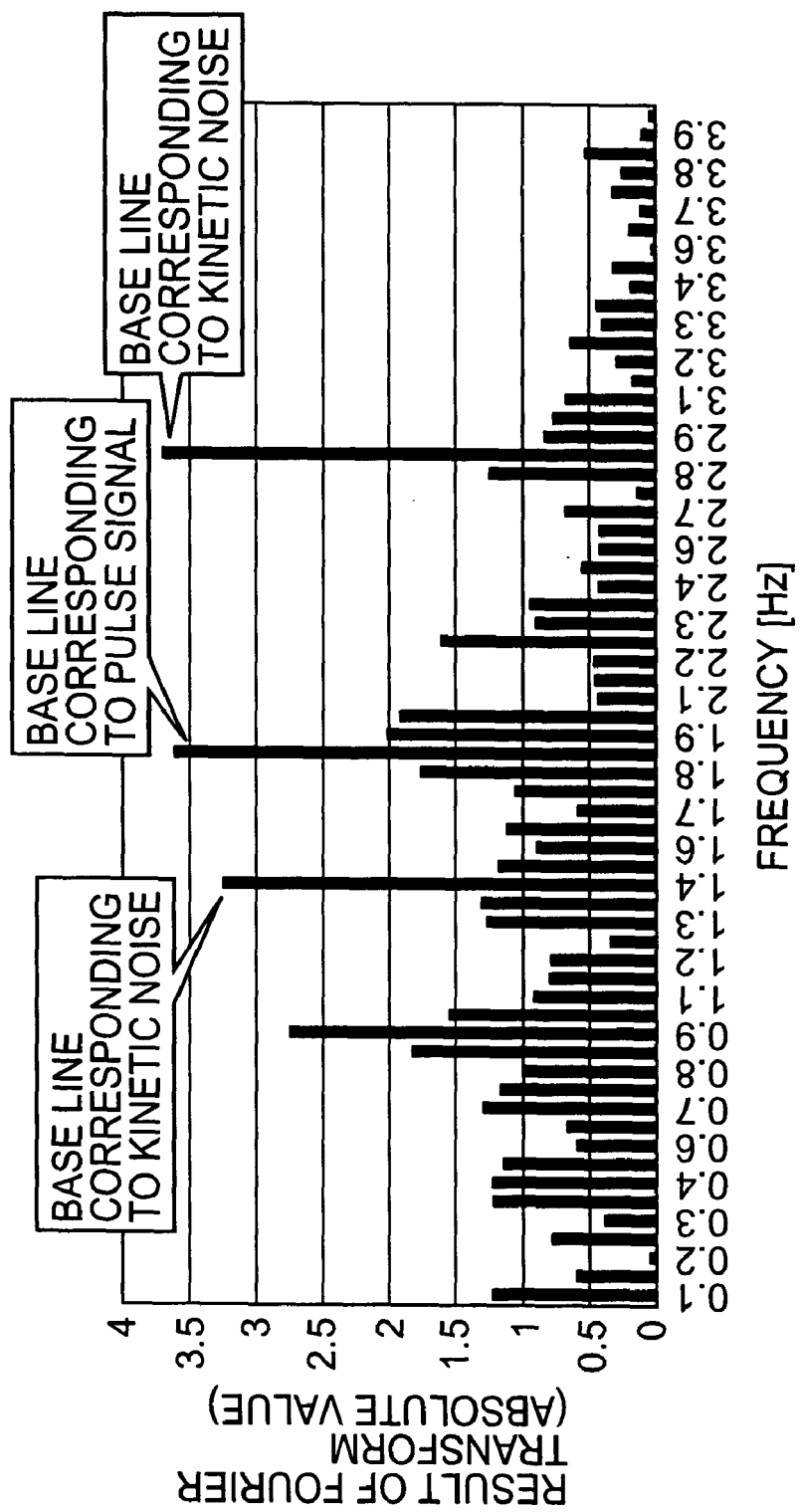
FIG. 7 is a waveform diagram for explaining a process in a pulse wave detecting apparatus according to the related art.

When the modified moving average process circuit 107 is deleted as in the pulse wave detecting apparatus according to the related art, the FFT circuit 108 outputs signals as shown in FIG. 7.

Let us compare the signal-to-noise ratios in FIGS. 4 and 7 based on the definition that a signal-to-noise ratio equals the sum of the heights of base lines corresponding to pulse signals and the heights of base lines before and after the same divided by the sum of the heights of all base lines. Then, the signal-to-noise ratios in FIGS. 4 and 7 are 0.145 and 0.123, respectively. Thus, the present embodiment including the modified moving average process circuit 107 provides a signal-to-noise ratio better than that of the pulse wave detecting apparatus according to the related art and allows highly accurate measurement by suppressing the influence of noises. Since the use of the modified moving average process circuit 107 makes it possible to reduce the number of data to be processed, loads on the Fourier transform circuit 108 and the pulse rate calculation circuit 113 can be reduced.

As described above, the pulse wave detecting apparatus of the present embodiment is characterized in that it has the pulse wave sensor 101 that detects a pulse wave of a subject and outputs pulse signals associated therewith, the A-D conversion circuit 106 that samples the pulse signals from the pulse wave sensor 101 at a first predetermined frequency and sequentially outputs resultant digital signals, the modified moving average process circuit 107 that sequentially averages every predetermined number of digital signals from the A-D conversion circuit 106 and sequentially outputs resultant signals at a second predetermined frequency, a Fourier transform circuit 108 that performs a Fourier transform process on the digital signals from the modified moving average process circuit 107, and the pulse rate calculation circuit 113 that calculates a pulse rate based on the result of the process at the Fourier transform circuit 108. Thus, since the signals are averaged by the modified moving average process circuit 107, highly accurate measurement can be carried out with the influence of noises suppressed. Further, since the number of data to be processed can be reduced, a pulse rate can be more accurately measured even when the calculating unit such as the Fourier transform circuit 108 and the pulse rate calculation circuit 113 has low calculating capability.

The pulse wave detecting apparatus of the present embodiment is also characterized in that it has the acceleration sensor 109 that detects kinetic noises and outputs noise signals associated therewith, the A-D conversion circuit 111 that samples the noise signals from the acceleration sensor 109 at the second frequency and sequentially outputs resultant signals, and the Fourier transform circuit 112 that performs a Fourier transform process on the signals from the A-D conversion circuit 111 and in that the pulse rate calculation circuit 113 calculates a pulse rate based on the signals output by the Fourier transform circuits 108 and 112. Thus, even when kinetic noises are generated by movements of a subject, the influence of the noises can be suppressed to allow highly accurate measurement.

The Fourier transform process apparatus of the present embodiment is characterized in that it has the A-D conversion circuit 106 that samples input signals at a first frequency and sequentially outputs resultant digital signals, the modified moving average process circuit 107 that sequentially averages every predetermined number of digital signals from the A-D conversion circuit 106 and sequentially outputs resultant signals at a second frequency, and the Fourier transform circuit 108 that performs a Forier transform process on the signals from the modified moving average process circuit 107. Therefore, a more accurate Fourier transform process can be carried out even when the Fourier transform circuit 108 has low calculating capability, which makes it possible to provide a Fourier transform process apparatus suitable for a pulse wave detecting apparatus that must be small-sized and capable of measuring a pulse rate accurately.

A configuration may be employed in which the first frequency is n times the second frequency (n is an integer equal to or greater than 2) and in which the modified moving average process circuit 107 sequentially averages every n signals input from the A-D conversion circuit 106 and sequentially outputs signals obtained through the averaging. A configuration may be employed in which the second frequency is $2^m$ Hz (m is a positive integer). This allows the FFT circuit 108 to perform its process quickly.

The modified moving average process circuit 107, the FFT circuits 108 and 112 and the pulse rate calculation circuit 113 may be constituted by a central processing unit (CPU).

When the pulse rate of a subject may be statically identified without consideration to movements of the subject, the acceleration sensor 109, the filter and amplifier circuit 110, the A-D conversion circuit 111, and the FFT circuit 112 are not required and, in this case, the pulse rate calculation circuit 113 calculates the pulse rate based on signals from the FFT circuit 108.

Figure 8:
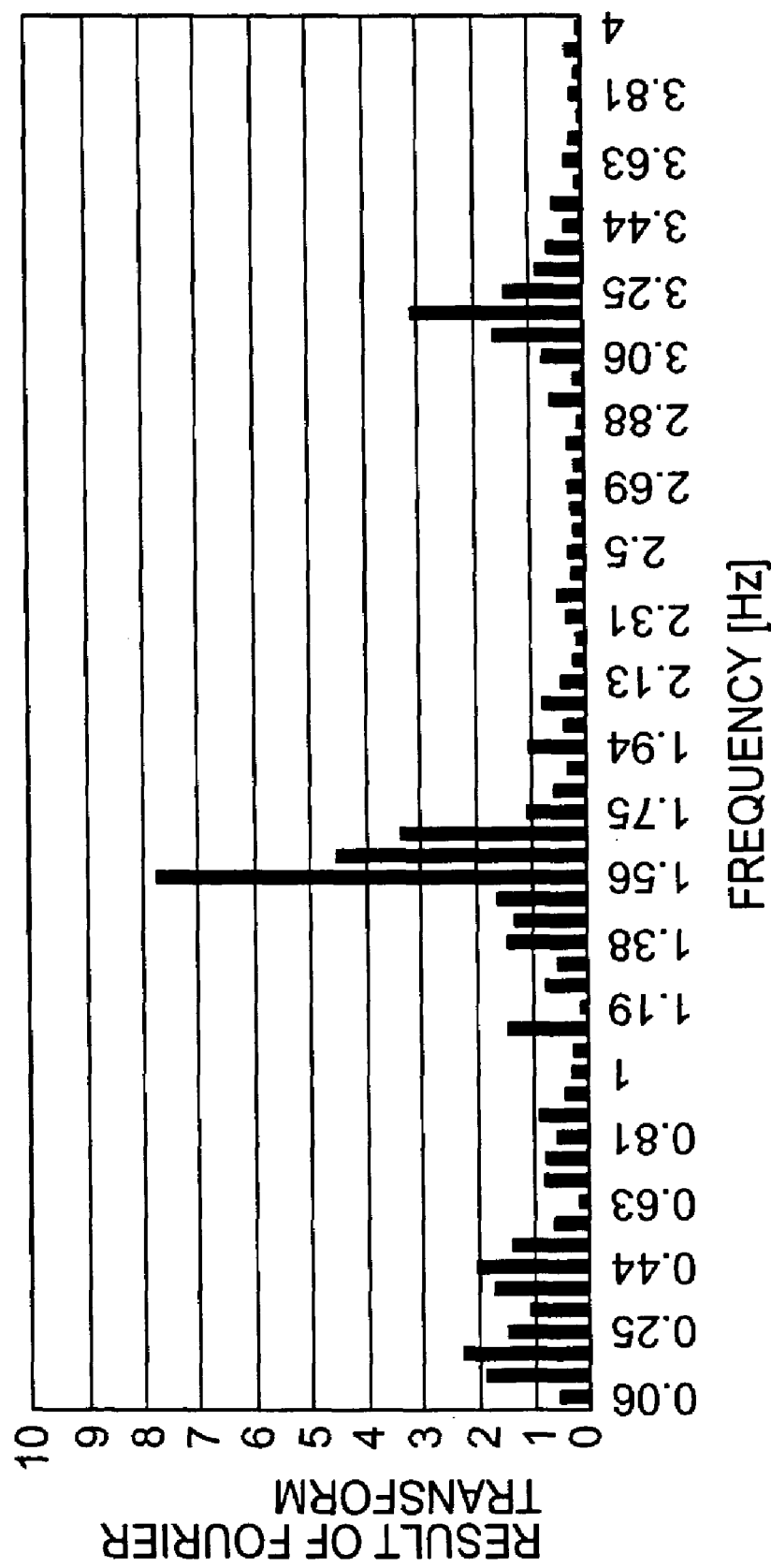
FIG. 8 is a waveform diagram for explaining a process in the embodiment of the invention.
Figure 9:
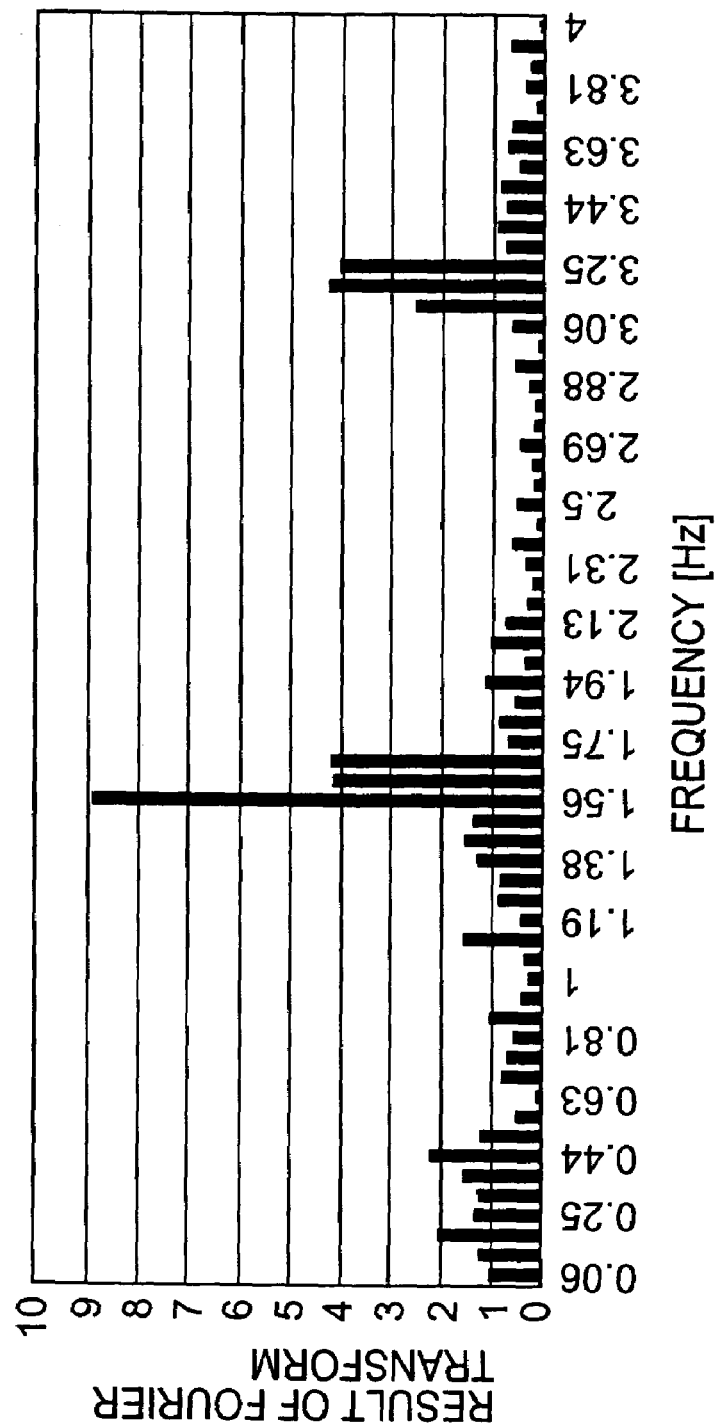
FIG. 9 is a waveform diagram for explaining a process in a pulse wave detecting apparatus according to the related art.

FIGS. 8 and 9 are waveform diagrams for explaining a process of identifying a pulse rate statically. FIG. 8 is a waveform diagram of signals that are statically obtained from the FFT circuit 108 of the pulse wave detecting apparatus in FIG. 1, and FIG. 9 is an output waveform diagram of an FFT circuit of a pulse wave detecting apparatus according to the related art which does not have the modified moving average process circuit 107.

Let us define that a signal-to-noise ratio equals the sum of the heights of base lines corresponding to pulse signals and the heights of base lines before and after the same divided by the sum of the heights of all base lines, just as mentioned above. Then, signal-to-noise ratios of 0.24 and 0.21 result from FIGS. 8 and 9, respectively. Thus, the present embodiment including the modified moving average process circuit 107 provides a signal-to-noise ratio better than that of the pulse wave detecting apparatus according to the related art and allows highly accurate measurement by suppressing the influence of noises.

The pulse wave detecting apparatus according to the invention allows more accurate measurement of a pulse rate even with a calculation unit having low calculating capability.

Further, the invention makes it possible to provide a Fourier transform process apparatus suitable for the pulse wave detecting apparatus that is capable of more accurate measurement of a pulse rate even with a calculation unit having low calculating capability.

What is claimed is:

1. A pulse wave detecting apparatus comprising:
    a signal detecting unit that detects a pulse wave and outputs pulse signals associated therewith;
    a signal sampling process unit that samples the pulse signals from the signal detecting unit at a first frequency and sequentially outputs resultant signals;
    an averaging process unit that sequentially averages without duplication every predetermined number of signals from the signal sampling process unit and sequentially outputs resultant signals at a second frequency which is lower than the first frequency;
    a signal Fourier transform process unit that performs a Fourier transform process on the signals from the averaging process unit; and
    a pulse rate calculation process unit that calculates a pulse rate based on the result of the process at the signal Fourier transform process unit.

2. A pulse wave detecting apparatus according to claim 1, further comprising;
    a noise detecting unit that detects kinetic noises and outputs noise signals associated therewith;
    a noise sampling process unit that samples the noise signals from the noise detecting unit at the second frequency and sequentially outputs resultant signals; and
    a noise Fourier transform process unit that performs a Fourier transform process on the signals from the noise sampling process unit;
    wherein the pulse rate calculation process unit calculates a pulse rate based on signals output by the signal Fourier transform process unit and the noise Fourier transform process unit.

3. A pulse wave detecting apparatus according to claim 1, wherein the first frequency is n times (n is an integer equal to or greater than 2) the second frequency and wherein the averaging process unit averages every n signals from the signal sampling process unit in the order of input and sequentially outputs signals obtained through the averaging.

4. A pulse wave detecting apparatus according to claim 1, wherein the second frequency is $2^m$ Hz (m is a positive integer).

* * * * *